(12) United States Patent
Vogler et al.

(10) Patent No.: US 7,858,208 B2
(45) Date of Patent: Dec. 28, 2010

(54) USE OF A COPPER (I) COMPLEXES FOR ORGANIC LUMINESCENT DIODES

(75) Inventors: Arnd Vogler, Regensburg (DE); Valeri Pawlowski, Regensburg (DE); Hans-Werner Schmidt, Bayreuth (DE); Mukundan Thelakkat, Bayreuth (DE); Markus Baete, Kulmain (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 812 days.

(21) Appl. No.: 11/575,554

(22) PCT Filed: Sep. 20, 2005

(86) PCT No.: PCT/EP2005/010122

§ 371 (c)(1),
(2), (4) Date: Mar. 19, 2007

(87) PCT Pub. No.: WO2006/032449

PCT Pub. Date: Mar. 30, 2006

(65) Prior Publication Data

US 2008/0199731 A1    Aug. 21, 2008

(30) Foreign Application Priority Data

Sep. 24, 2004    (DE) ................ 10 2004 046 665

(51) Int. Cl.
*H01J 1/63*    (2006.01)
*C07F 9/28*    (2006.01)

(52) U.S. Cl. ..................... 428/690; 427/58; 427/66; 544/225

(58) Field of Classification Search ............. 428/690; 544/225; 427/58, 66
See application file for complete search history.

(56) References Cited

U.S. PATENT DOCUMENTS

| 2002/0182441 | A1 | 12/2002 | Lamansky et al. |
| 2005/0014024 | A1* | 1/2005 | Tsuboyama et al. ......... 428/690 |
| 2005/0079384 | A1 | 4/2005 | Tsuboyama et al. |

FOREIGN PATENT DOCUMENTS

WO    03 095587    11/2003

OTHER PUBLICATIONS

Garcia-Seijo M. I.; Sevillano P.; Gould, R. O.; Fernandez-Anca, D.; Garcia-Fernandez M. E. Inrog. Chim. Acta., 2003, 353, 206-216.*

(Continued)

*Primary Examiner*—D. Lawrence Tarazano
*Assistant Examiner*—J. L. Yang
(74) *Attorney, Agent, or Firm*—Oblon, Spivak, McClelland, Maier & Neustadt, L.L.P.

(57) ABSTRACT

The present invention relates to the use of copper(I) complexes of the formula I

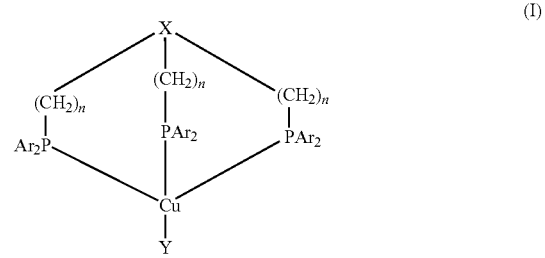

(I)

where
X is nitrogen or a C—R group,
R is alkyl or aryl,
Ar is phenyl or naphthyl, each of which is optionally substituted by from one to three radicals selected from the group consisting of alkoxy, alkylthio, alkylamino, dialkylamino, alkoxycarbonyl, alkoxysulfonyl, halogen, cyano, carboxyl, hydroxysulfonyl and nitro, and the two optionally substituted phenyl or naphthyl radicals may be joined to one another by a chemical single bond via the carbon atoms in the α- and α'-position relative to the phosphorus atom,
n is 1, 2 or 3,
and
Y is halogen, cyano, thiocyanato, alkoxy, aryloxy, alkylthio, arylthio, alkylamino, dialkylamino, arylamino or diarylamino,
in organic light-emitting diodes (OLEDs), The present invention further relates to light-emitting layers which comprise at least one copper(I) complex of the formula I, to OLEDs which comprise at least one copper(I) complex of the formula I or an inventive light-emitting layer, and to stationary visual display units which comprise inventive OLEDs.

Furthermore, the present invention relates to novel copper(I) complexes of the formula Ia and Ib

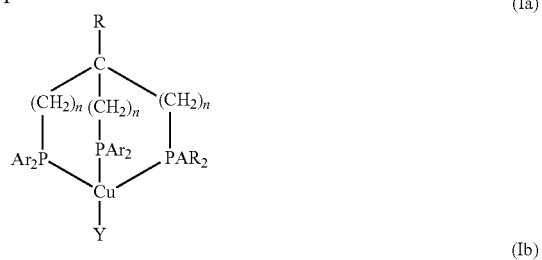

(Ia)

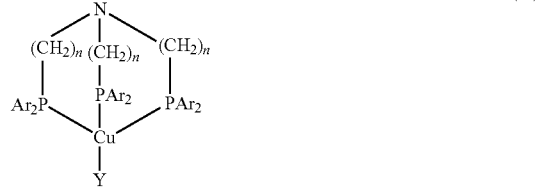

(Ib)

where R, Ar and n are each as defined in formula I, Y in formula Ia is defined as cyano, thiocyanato, alkoxy, aryloxy, alkylthio, arylthio, alkylamino, dialkylamino, arylamino or diarylamino, and Y in formula Ib is defined as halogen, cyano, thiocyanato, alkoxy, aryloxy, alkylthio, arylthio, alkylamino, dialkylamino, arylamino or diarylamino.

14 Claims, No Drawings

OTHER PUBLICATIONS

Eller, P. G.; Kubas, G. J. J. Am. Chem. Soc., 1977, 13, 4346-4351.*

Fackler, J. P.; Forward, J. M.; Grant, T.; Staples, R. J. J. Mol. Struc., 1998, 470, 151-160.*

Sacconi, L.; Ghilardi, C. A.; Mealli, C.; Zanobini, F. Inorg. Chem. (1975), 14(6), 1380-6.*

Zumbulyadis, N.; Gysling, H. J. J. Am. Chem. Soc. 1982, 104, 3246-3247.*

Ma, Yuguang et al.,"High Luminescence Gold(I) and Copper(I) Complexes with a Triplet Excited State for Use in Light-Emitting Diodes", Adv. Mater., vol. 11, No. 10, pp. 852-857, 1999.

Zhang, Qisheng et al.,"Highly Efficient Green Phosphorescent Organic Light-Emitting Diodes Based on $Cu^I$ Complexes", Adv. Mater., vol. 16, No. 5, pp. 432-436, 2004.

Sacconi, L. et al.,"Halogeno-Complexes of Cobalt(I) and Nickel(I) with 1,1,1-tris(diphenyl-phosphinomethyl)ethane", J.C.S. Dalton, pp. 1213-1216, 1972.

Fackler, John P. et al.,"Structural and Spectroscopic Comparisons of tris(2-(diphenylphosphino)ethyl)aminecopper(I) tetraphenylborate, [$(NP_3)Cu$]($BPh_4$), with Gold(I) and Silver(I) [$(NP_3)M$]X(X=$BPh_4$, $NO_3$, $PF_6$) Complexes", Journal of Molecular Structure, vol. 470, pp. 151-160, 1998.

* cited by examiner

USE OF A COPPER (I) COMPLEXES FOR ORGANIC LUMINESCENT DIODES

The present invention relates to the use of copper(I) complexes of the formula I

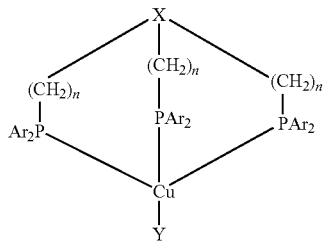

(I)

where
X is nitrogen or a C—R group,
R is alkyl or aryl,
Ar is phenyl or naphthyl, each of which is optionally substituted by from one to three radicals selected from the group consisting of alkoxy, alkylthio, alkylamino, dialkylamino, alkoxycarbonyl, alkoxysulfonyl, halogen, cyano, carboxyl, hydroxysulfonyl and nitro, and the two optionally substituted phenyl or naphthyl radicals may be joined to one another by a chemical single bond via the carbon atoms in the α- and α'-position relative to the phosphorus atom,
n is 1, 2 or 3, and
Y is halogen, cyano, thiocyanato, alkoxy, aryloxy, alkylthio, arylthio, alkylamino, dialkylamino, arylamino or diarylamino in organic light-emitting diodes (OLEDs).

The present invention further relates to light-emitting layers which comprise at least one copper(I) complex of the formula I, to OLEDs which comprise at least one The present invention further relates to light-emitting layers which comprise at least one copper(I) complex of the formula I, to OLEDs which comprise at least one copper(I) complex of the formula I or an inventive light-emitting layer, and to stationary visual display units which comprise inventive OLEDs.

Furthermore, the present invention relates to novel copper (I) complexes of the formula Ia and Ib

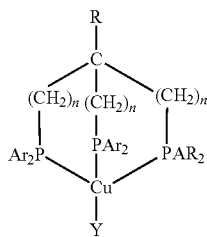

(Ia)

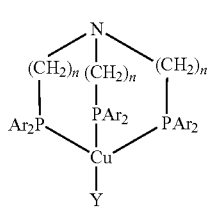

(Ib)

where R, Ar and n are each as defined in formula I, Y in formula Ia is defined as cyano, thiocyanato, alkoxy, aryloxy, alkylthio, arylthio, alkylamino, dialkylamino, arylamino or diarylamino, and Y in formula Ib is defined as halogen, cyano, thiocyanato, alkoxy, aryloxy, alkylthio, arylthio, alkylamino, dialkylamino, arylamino or diarylamino.

In OLEDs, the property of materials to emit light when they are excited by electrical current is utilized. OLEDs are of particular interest as an alternative to cathode ray tubes and liquid crystal displays for the production of flat visual display units. Owing to the very compact design and the intrinsically relatively low electricity consumption, devices which comprise OLEDs are suitable in particular for mobile applications, for instance in mobile telephones, laptops, etc.

Numerous materials have been proposed which emit light on excitation by electrical current (electroluminescence). However, copper complexes of the formula I have not yet been described in the application for OLEDs.

Investigations of Qisheng Zhang et al (Adv. Mater. 2004, 16, No. 5, 432-436) on copper(I) complexes which have bidentate phenanthroline derivatives and either two (monodentate) triphenylphosphine molecules or bidentate triphenylphosphine dimers bridged by an ether function as complex ligands on the copper center show the suitability of these compounds for applications in OLEDs.

Structural and spectroscopic comparisons of tris(2-diphenylphosphino)ethylamine-copper(I) tetraphenylborates to the corresponding gold(I) and silver(I) complexes have been carried out by John P. Fackler et al. (J. Mol. Structure. 470 (1998), 151-160) The authors found sometimes strong luminescence in the gold complexes investigated, but not in the copper and silver complexes.

L. Sacconi and S. Midollini (J. Chem. Soc. Dalton Trans. 1972, 1213-1216) describe the synthesis of halogen complexes of cobalt(I), nickel(I) and copper(I) with 1,1,1-tris (diphenylphosphinomethyl)ethane.

However, the two aforementioned publications do not give any indication of the possible suitability of the copper complexes in question for applications in OLEDs.

It is therefore an object of the present application to provide a further compound class which is suitable for use in different layers of an OLED, in particular to provide compounds which have electroluminescence in the blue and green region, but also, with regard to the production of full-color displays, in the red region of the electromagnetic spectrum.

This object is achieved by the use of the copper complexes of the formula I shown at the outset in OLEDs.

The copper(I) complexes of the formula I may be used in the light-emitting layer of an OLED as an emitter substance or as matrix materials for emitter substances. It is additionally possible to use the copper(I) complexes as electron blockers, for example, in a blocking layer for electrons which is disposed between a light-emitting layer and a hole-transporting layer of the OLED. Preference is given to using the copper(I) complexes as emitter molecules in the light-emitting layer.

In the context of the present application, alkyl, aryl and aralkyl, alkoxy, alkylthio, alkylamino, dialkylamino, alkyloxycarbonyl, alkyloxysulfonyl radical or group, alkyl radical or group, alkoxy radical or group and aryloxy radical or group are defined as follows:

Aryl is a radical having a basic skeleton of from 6 to 30 carbon atoms, preferably from 6 to 18 carbon atoms, which is formed from one aromatic ring or a plurality of fused aromatic rings, Suitable basic skeletons are, for example, phenyl, naphthyl, anthracenyl or phenanthrenyl. This basic skeleton may be unsubstituted (i.e. all carbon atoms which are substitutable bear hydrogen atoms) or be substituted at one, more than one or all substitutable positions of the basic skeleton, Suitable substituents are, for example:
alkyl radicals, preferably alkyl radicals having from 1 to 8 carbon atoms, more preferably methyl, ethyl, i-propyl or t-butyl,
aryl radicals, preferably $C_6$ aryl radicals, which may in turn be substituted or unsubstituted,
heteroaryl radicals, preferably heteroaryl radicals which contain at least one nitrogen atom, more preferably pyridyl radicals,
alkenyl radicals, preferably alkenyl radicals which bear one double bond, more preferably alkenyl radicals having one double bond and from 1 to 8 carbon atoms, or groups having donor or acceptor action.

Groups having donor action refer to groups which have a +I and/or +M effect, and groups having acceptor action to groups which have a −I and/or −M effect. Suitable groups having donor or acceptor action are halogen radicals, preferably F, Cl, Br, more preferably F, alkoxy radicals, carbonyl radicals, ester radicals, amine radicals, amide radicals, $CH_2F$ groups, $CHF_2$ groups, $CF_3$ groups, CN groups, thio groups or SCN groups.

Particular preference is given to aryl being substituted by radicals selected from the group consisting of methyl, F, Cl and alkoxy, or to aryl being unsubstituted.

Aryl is preferably a $C_6$ aryl radical which is optionally substituted by at least one of the aforementioned substituents. The $C_6$ aryl radical more preferably has none, one or two of the aforementioned substituents, one substituent preferably being arranged in the para-position to the further linking point of the aryl radical and, in the case of two substituents, they are each arranged in the meta-position to the further linking point of the aryl radical.

The $C_6$ aryl radical is very particularly preferably an unsubstituted phenyl radical.

Alkyl refers to a radical having from 1 to 20 carbon atoms, preferably from 1 to 10 carbon atoms, more preferably from 1 to 8 carbon atoms, The alkyl may be branched or unbranched, and optionally be interrupted by one or more heteroatoms, preferably N, O or S. In addition, the alkyl may be substituted by one or more of the substituents mentioned under aryl. It is likewise possible that the alkyl bears one or more aryl groups. In this context, all of the above-listed aryl groups are suitable. In addition, the alkyl may be a cyclic alkyl having from 3 to 10 ring atoms, preferably from 4 to 7 ring atoms. The ring atoms are carbon atoms, of which one or more carbon atoms may be replaced by heteroatoms, preferably N, O or S. The cyclic alkyl may be substituted by branched or unbranched alkyl radicals.

Preferred alkyl is selected from the group consisting of methyl, ethyl, i-propyl, n-propyl, i-butyl, n-butyl, t-butyl, sec-butyl, i-pentyl, n-pentyl, sec-pentyl, neopentyl, n-hexyl, i-hexyl and sec-hexyl, cyclohexyl and cyclopentyl.

Particularly preferred alkyl is methyl, i-propyl, t-butyl and n-hexyl,

Alkoxy refers to a group of the general formula —$OR^1$ where $R^1$ is alkyl as defined above. Preferred alkoxy is thus selected from the group consisting of —Omethyl, —Oethyl, —$O^i$propyl, —$O^n$propyl, —$O^i$butyl, —$O^n$butyl, —$O^t$butyl, —$O^{sec}$butyl, —$O^i$pentyl, —$O^n$pentyl, —$O^{sec}$pentyl, —$O^{neo}$pentyl, —$O^n$hexyl, —$O^i$hexyl and —$O^{sec}$hexyl.

Particularly preferred alkoxy is —Omethyl, —$O^i$propyl, —$O^t$butyl and —$O^n$hexyl. Aryloxy refers to a group of the general formula —$OR^2$ where $R^2$ is aryl as defined above. Particularly preferred as aryloxy is an —Ophenyl radical.

Alkylthio refers to a group of the general formula —$SR^3$ where $R^3$ is alkyl as defined above. Preferred alkylthio is thus selected from the group consisting of —Smethyl, —Sethyl, —$S^i$propyl, —$S^n$propyl, —$S^i$butyl, $S^n$butyl, —$S^t$butyl, —$S^{sec}$butyl, —$S^i$pentyl, —$S^n$pentyl, —$S^{sec}$pentyl, —$S^{neo}$pentyl, —$S^n$hexyl, —$S^i$hexyl and —$S^{sec}$hexyl. Alkylthio is more preferably —Smethyl, —$S^i$propyl, —$S^t$butyl and —$S^n$hexyl.

Arylthio refers to a group of the general formula —$SR^4$ where $R^4$ is aryl as defined above. Arylthio is more preferably an —Sphenyl radical.

Alkylamino refers to a group of the general formula —$NHR^5$ where $R^5$ is alkyl as defined above. Preferred alkylamino is thus selected from the group consisting of —NHmethyl, —NHethyl, —$NH^i$propyl, —$NH^n$propyl, —$NH^i$butyl, —$NH^n$butyl, —$NH^t$butyl, —$NH^{sec}$butyl, —$NH^i$pentyl, —$NH^n$pentyl, —$NH^{neo}$pentyl —$NH^n$hexyl, —$NH^i$hexyl and —$NH^{sec}$hexyl. Alkylthio is more preferably —NHmethyl, —$NH^i$propyl, —$NH^t$butyl and —$NH^n$hexyl.

Arylamino refers to a group of the general formula —$NHR^6$ where $R^6$ is aryl as defined above. Arylamino is more preferably an —NHphenyl radical.

Dialkylamino refers to a group of the general formula —$NR^7R^8$ where $R^7$ and $R^8$ are each independently alkyl as defined above. Preferred dialkylamino —$NR^7R^8$ contains $R^7$ and $R^8$ radicals which are each independently selected from the group consisting of methyl, ethyl, i-propyl, n-propyl, i-butyl, n-butyl t-butyl, sec-butyl, i-pentyl, n-pentyl, sec-pentyl, neopentyl, n-hexyl, i-hexyl and sec-hexyl, cyclohexyl and cyclopentyl. The $R^7$ and $R^8$ radicals are preferably the same.

Diarylamino refers to a group of the general formula —$NR^9R^{10}$ where $R^9$ and $R^{10}$ are each independently aryl as defined above. The $R^9$ and $R^{10}$ radicals are preferably the same. Diarylamino is more preferably an —$N(phenyl)_2$ radical.

Alkoxycarbonyl refers to a group of the general formula —$(CO)OR^{11}$ where $R^{11}$ is alkyl as defined above. Preferred alkoxycarbonyl is thus selected from the group consisting of —(CO)Omethyl, —(CO)Oethyl, —$(CO)O^i$propyl, —$(CO)O^n$propyl, —$(CO)O^i$butyl, —$(CO)O^n$butyl, —$(CO)O^t$butyl, —$(CO)O^{sec}$butyl, —$(CO)O^i$pentyl, —$(CO)O^n$pentyl, —$(CO)O^{sec}$pentyl, —$(CO)O^{neo}$pentyl, —$(CO)O^n$hexyl, —$(CO)O^i$hexyl and —$(CO)O^{sec}$hexyl.

Particularly preferred alkoxycarbonyl is —(CO)Omethyl, —$(CO)O^i$propyl, —$(CO)O^t$butyl and —$(CO)O^n$hexyl.

Alkoxysulfonyl refers to a group of the general formula —$(SO_2)OR^{12}$ where $R^{12}$ is alkyl as defined above. Preferred alkoxysulfonyl is thus selected from the group consisting of —$(SO_2)$Omethyl, —$(SO_2)$Oethyl, —$(SO_2)O^i$propyl, —$(SO_2)O^n$propyl, —$(SO_2)O^i$butyl, —$(SO_2)O^n$butyl, —$(SO_2)O^t$butyl, —$(SO_2)O^{sec}$butyl, —$(SO_2)O^i$pentyl, —$(SO_2)O^n$pentyl, —$(SO_2)O^{sec}$pentyl, —$(SO_2)O^{neo}$pentyl, —$(SO_2)O^n$hexyl, —$(SO_2)O^i$hexyl and —$(SO_2)O^{sec}$hexyl.

Particularly preferred alkoxysulfonyl is —$(SO_2)$Omethyl, —$(SO_2)O^i$propyl, —$SO_2)O^t$butyl and —$(SO_2)O^n$hexyl.

Halogen is preferably F, Cl or Br, more preferably Cl or Br.

When the variables Ar together refer to two phenyl or naphthyl radicals which are joined to one another by a chemical single bond via the carbon atoms in the α- and α'-position relative to the phosphorus atom, this results, instead of the —$Ar_2P$— units in the formulae I, Ia and Ib, in the units shown below:

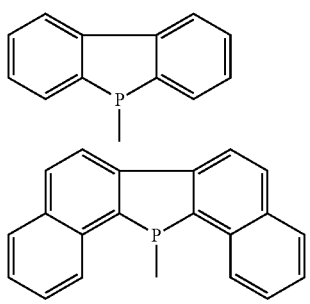

These units may optionally also be substituted on the rings by the aforementioned groups.

The three values 1, 2 or 3 for n in the formula I may be different from one another but are preferably the same.

Preference is given in accordance with the invention to using compounds of the formula I in which n assumes values of 1 or 2.

In particular, compounds of the formula I in which either three methylene or three ethylene bridges are present between X and P are therefore used with preference.

In a further embodiment, preference is given in accordance with the invention to using compounds of the formula I in which X is a C—R group, and reference is made to the details above with regard to the definition of R as alkyl or aryl.

In particular, R in the C—R group is defined as alkyl as detailed above.

The aforementioned copper(I) complexes of the formula I and their preferred embodiments are outstandingly suitable as emitter molecules in OLEDs. Simple variations of the ligands make it possible to provide copper(I) complexes which exhibit electroluminescence in the green and in particular in the blue range of the electromagnetic spectrum. The copper(I) complexes used in accordance with the invention are suitable, together with appropriate further emitters, for use in industrially usable full-color displays.

The copper(I) complexes are prepared by processes known to those skilled in the art. In particular, reference is made here to the literature citations and the references therein mentioned at the outset. Essentially, the complexes are obtained according to the following general reaction equation:

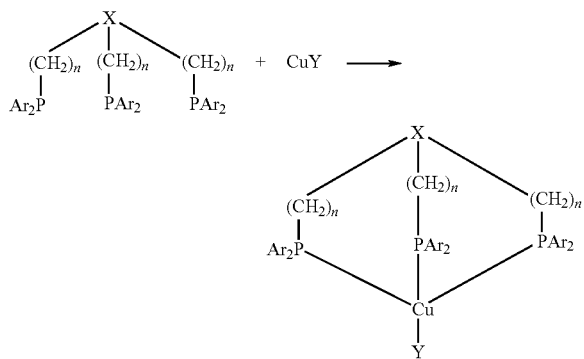

For the preparation of corresponding tridentate ligands, reference is made, for example, to H. Seidel, G. Huttner and G. Helmchen, Z. Naturforsch. 48 b, 1681-1692 (1993), T. Seitz, A. Muth and G. Huttner, Chem. Ber. 127 (1994) 1837-1842, H. Seidel, G. Huttner and L. Zsolnai, Z. Naturforsch. 50 b, 729-734 (1995) and T. Seitz, A. Muth and G. Huttner, Z. Naturforsch. 50 b, 1045-1049 (1995).

Complexes in which Y is different from halogen, cyanato or thiocyanato may be prepared, for example, starting from the halogen-containing copper(I) complexes of the formula I by anion exchange. These exchange reactions too are familiar to those skilled in the art and can be schematized in the following reaction equation:

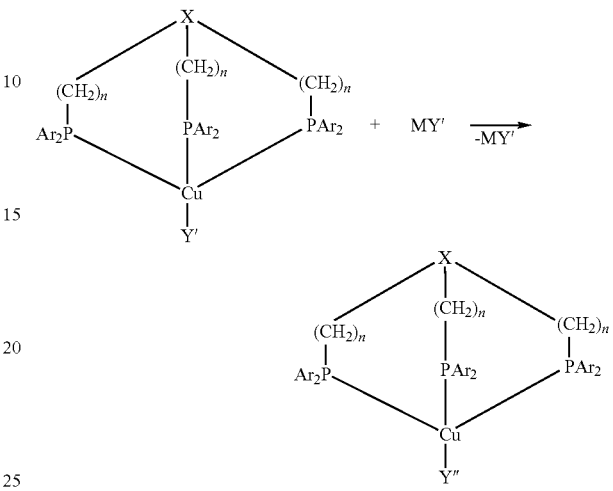

Y' is, for example, chlorine or bromine, Y" is the anion corresponding to the alkoxy, aryloxy, alkylthio, arylthio, alkylamino, dialkylamino, arylamino or diarylamino radical, and M is a monovalent metal, for instance silver(I) or an alkali metal, e.g. sodium or potassium.

The reaction is effected preferably in solution or suspension. Suitable solvents are in particular aprotic solvents known to those skilled in the art, for instance toluene or benzene, ethers, e.g. tetrahydrofuran, tert-butyl ether or tert-butyl methyl ether, acetonitrile or halogenated hydrocarbons, for example methylene chloride.

The molar ratio of copper(I) compound CuY used to ligand used is typically from 0.7:1.0 to 1.5:1.0, preferably from 0.9:1.0 to 1.1:1.0 and in particular 1:1.

The resulting copper(I) complex of the formula I is worked up by customary methods of organometallic synthesis which are known to those skilled in the art.

The copper(I) complexes of the formula I used in accordance with the invention are outstandingly suitable as emitter substances, since they have emission (electroluminescence) in the visible region of the electromagnetic spectrum. With the aid of the copper(I) complexes as emitter substances, it is possible in particular to generate electroluminescence in the blue and green region of the electromagnetic spectrum. In addition, the copper(I) complexes are suitable as electron blockers, for example in a blocking layer for electrons in an OLED which is disposed between the light-emitting layer and a hoe-transporting layer of the OLED.

A special property of the copper(I) complexes of the formula I is that they exhibit luminescence, in particular electroluminescence, in the visible region of the electromagnetic spectrum in the solid state too. Therefore, these complexes may be used in substance, without further additives, as emitter substances in OLEDs. The production of an OLED with a light-emitting layer is accordingly possible without complicated coevaporation of a matrix material with the emitter substance.

The present application therefore further provides organic light-emitting diodes (OLEDs) comprising at least one copper(I) complex of the formula I.

Organic light-emitting diodes are in principle composed of several layers:
1. Anode
2. Hole-transporting layer
3. Light-emitting layer
4. Electron-transporting layer
5. Cathode The copper(I) complexes may be used in different layers of the OLED depending on the position of their HOMO; for example, the copper(I) complexes may be used as electron blockers in a blocking layer for electrons or as emitter molecules in the light-emitting layer.

Preference is given to using them as emitter molecules in the light-emitting layer.

The present application therefore also provides a light-emitting layer comprising at least one copper(I) complex of the formula I. The present application further provides an organic light-emitting diode which comprises such a light-emitting layer.

Preferred copper(I) complexes have already been specified above.

The copper(I) complexes used in accordance with the invention may be used in substance, without further additives, in the light-emitting layer. However, it is likewise possible that further compounds are present in the light-emitting layer in addition to the copper(I) complexes used in accordance with the invention. For example, a fluorescent dye may be present in order to alter the emission color of the copper(I) complex used as an emitter molecule. A dilution material may additionally be used. This dilution material may be a polymer, for example poly(N-vinylcarbazole) or polysilane. However, the dilution material may likewise be a small molecule, for example 4, 4'-N,N'-dicarbazolebiphenyl (CBP), tetrearyisilane or tertiary aromatic amines. When a dilution material is used, the proportion of the copper(I) complexes used in accordance with the invention in the light-emitting layer is generally less than 20% by weight, preferably from 3 to 10% by weight. Preference is given to using the copper(I) complexes in substance, which avoids a complicated coevaporation of the copper(I) complexes with a matrix material (dilution material or fluorescent dye). For this purpose, it is essential that the copper(I) complexes luminesce in the solid state, which is in fact the case for these complexes. Thus, the light-emitting layer preferably comprises at least one copper(I) complex of the formula I and no further matrix material, for instance dilution material and/or fluorescent dye.

The individual aforementioned layers of the OLED may be composed of 2 or more layers. For example, the hole-transporting layer may be composed of one layer into which holes are injected from the electrode and one layer which transports the holes from the hole-injecting layer away into the light-emitting layer. The electron-transporting layer may likewise consist of a plurality of layers, for example one layer in which electrons are injected by the electrode and one layer which receives electrons from the electron-injecting layer and transports them into the light-emitting layer. These layers mentioned are each selected according to factors such as energy level, thermal resistance and charge carrier mobility, and also energy differential of the layers mentioned with the organic layers or the metal electrodes. Those skilled in the art are capable of selecting the structure of the OLEDs in such a way that it is adapted optimally to the copper(I) complexes used as emitter substances in accordance with the invention.

In order to obtain particularly efficient OLEDs, the HOMO (highest occupied molecular orbital) of the hole-transporting layer should be aligned to the work function of the anode, and the LUMO (lowest unoccupied molecular orbital) of the electron-transporting layer aligned to the work function of the cathode.

The anode (1) is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals include the metals of groups Ib, IVa, Va and VIa of the Periodic Table of the Elements, and also the transition metals of group VII. When the anode is to be transparent, mixed metal oxides of groups IIb, IIIb and IVb of the Periodic Table of the Elements are generally used, for example indium tin oxide (ITO), It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to decouple the light formed. Suitable hole-transport materials for the layer (2) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole-transport material, Customarily used hole-transporting molecules are selected from the group consisting of 4,4'-bis[N-(1-naphthyl)-N-phenylamino]biphenyl (α-NPD), N,N'-diphenyl-N,N'-bis(3-methylphenyl)-[1'-biphenyl]-4,4'-diamine (TPD), 1,1-bis[(di-4-tolylamino)phenyl]cyclohexane (TAPC), N N'-bis(4-methylphenyl)-N,N'-bis(4-ethylphenyl)-[1,1'-(3,3'-dimethy)biphenyl]-4,4'-diamine (ETPID), tetrakis-(3-methylphenyl)-N,N,N',N'-2,5-phenylenediamine (PDA), -phenyl-4-N,N-diphenylamino-styrene (TPS), p-(diethylamino)benzaldehyde diphenylhydrazone (DEH), triphenylamine (TPA), bis[4-N N-diethylamino)-2-methylphenyl)](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB) and porphyrine compounds such as copper phthalocyanines. Customarily used hole-transporting polymers are selected from the group consisting of polyvinylcarbazoles, (phenylmethyl) polysilanes and polyanilines. It is likewise possible to obtain hole-transporting polymers by doping hole-transporting molecules into polymers such as polystyrene and polycarbonate Suitable hole-transporting molecules are the molecules already mentioned above.

Suitable electron-transporting materials for the layer (4) of the inventive OLEDs include metals chelated with oxinoid compounds such as tris(8-quinolinolato)aluminum ($Alq_3$) compounds based on phenanthroline such as 2,9-dimethyl-4, 7-diphenyl-1,10-phenanthroline (BCP) or 4,7-diphenyl-1, 10-phenanthroline (DPA) and azole compounds such as 2-(4-biphenylyl)-5-(4-A-butylphenyl)-1,3,4-oxadiazole (PBD) and 3-(4-biphenylyl)-4-phenyl-5-(4-t-butylphenyl)-1,2,4-triazole (TAZ). The layer (4) may serve both to ease the electron transport and as a buffer layer or as a barrier layer in order to prevent quenching of the exciton at the interfaces of the layers of the OLED. The layer (4) preferably improves the mobility of the electrons and reduces quenching of the exciton.

The cathode (5) is an electrode which serves to introduce electrons or negative charge carriers. The cathode may be any metal or nonmetal which has a lower work function than the anode. Suitable materials for the cathode are selected from the group consisting of alkali metals of group Ia, for example Li, Cs, alkali earth metals of group IIa, metals of group IIb of the Periodic Table of the Elements, and the rare earth metals and the lanthanides and actinides. In addition, metals such as aluminum indium calcium barium, samarium and magnesium, and combinations thereof, may be used. In addition, lithium-containing organometallic compounds or LiF may be applied between the organic layer and the cathode in order to reduce the operating voltage.

The OLED of the present invention may additionally comprise further layers which are known to those skilled in the art. For example, a layer may be applied between the layer (2) and the light-emitting layer (3) which eases the transport of the positive charge and/or matches the band gaps of the layers to one another. Alternatively, this further layer may serve as a protective layer. In an analogous manner, additional layers may be present between the light-emitting layer (3) and the layer (4) in order to ease the transport of the negative charge and/or to match the band gaps between the layers to one another. Alternatively, this layer may also serve as a protective layer.

In a preferred embodiment, the inventive OLED, in addition to layers (1) to (5), comprises at least one of the further layers mentioned below:

a hole injection layer between the anode (1) and the hole-transporting layer (2);

a blocking layer for electrons between the hole-transporting layer (2) and the light-emitting layer (3);

a blocking layer for holes between the light-emitting layer (3) and the electron-transporting layer 4);

an electron injection layer between the electron-transporting layer (4) and the cathode (5).

Those skilled in the art know how suitable materials have to be selected (for example on the basis of electrochemical investigations). Suitable materials for the individual layers are known to those skilled in the art and disclosed, for example, in WO 00/70655.

Furthermore, each of the layers mentioned of the inventive OLED may be composed of two or more layers. In addition, it is possible that some or all of the layers (1), (2), (3), (4) and (5) have been surface-treated in order to increase the efficiency of charge carrier transport. The selection of the materials for each of the layers mentioned is preferably determined by obtaining an OLED having a high efficiency.

The inventive OLED may be produced by methods known to those skilled in the art. In general, the OLED is produced by successive vapor deposition of the individual layers onto a suitable substrate. Suitable substrates are, for example, glass or polymer films. For the vapor deposition, customary techniques may be used, such as thermal evaporation, chemical vapor deposition and others. In an alternative process, the organic layers may be coated from solutions or dispersions in suitable solvents, in which case coating techniques known to those skilled in the art are employed.

In general, the different layers have the following thicknesses: anode (2) from 500 to 5000 Å, preferably from 1000 to 2000 Å; hole-transporting layer (3) from 50 to 1000 Å, preferably from 200 to 800 Å; light-emitting layer (4) from 10 to 1000 Å, preferably from 100 to 800 Å; electron-transporting layer (5) from 50 to 1000 Å, preferably from 200 to 800 Å; cathode (6) from 200 to 1000 Å, preferably from 300 to 5000 Å. The location of the recombination zone of holes and electrons in the inventive OLED and thus the emission spectrum of the OLED may be influenced by the relative thickness of each layer. This means that the thickness of the electron transport layer should preferably be selected such that the electron/hole recombination zone is within the light-emitting layer. The ratio of the layer thicknesses of the individual layers in the OLED is dependent upon the materials used. The layer thicknesses of any additional layers used are known to those skilled in the art.

Use of the copper(I) complexes used in accordance with the invention as emitter molecules in the light-emitting layer of the inventive OLEDs allows OLEDs having a high efficiency to be obtained. The efficiency of the inventive OLEDs may additionally be improved by optimizing the other layers. For example, highly efficient cathodes such as Ca, Ba or LiF may be used. Shaped substrates and novel hole-transporting materials which bring about a reduction in the operating voltage or an increase in the quantum efficiency are likewise usable in the inventive OLEDs. Furthermore, additional layers may be present in the OLEDs in order to adjust the energy level of the different layers and to ease electroluminescence.

The inventive OLEDs may be used in all devices in which electroluminescence is useful. Suitable devices are preferably selected from stationary and mobile visual display units (VDUs). Stationary VDUs are, for example, VDUs of computers, televisions, VDUs in printers, kitchen appliances and advertising boards, illuminations and information boards. Mobile VDUs are, for example, VDUs in mobile telephones, laptops, vehicles and destination displays on buses and trains.

In addition, the copper(I) complexes used in accordance with the invention may be used with an inverse structure in OLEDs. In these inverse OLEDs, preference is given to using the copper(I) complexes in turn in the light-emitting layer, more preferably as the light-emitting layer without further additives. The structure of inverse OLEDs and the materials customarily used therein are known to those skilled in the art.

The present application further provides novel copper(I) complexes of the formula Ia

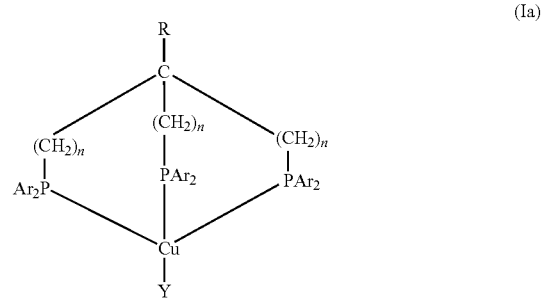

(Ia)

where

R is alkyl or aryl,

Ar is phenyl or naphthyl, each of which is optionally substituted by from one to three radicals selected from the group consisting of alkoxy, alkylthio, alkylamino, dialkylamino, alkoxycarbonyl, alkoxysulfonyl, halogen, cyano, carboxyl, hydroxysulfonyl and nitro, and the two optionally substituted phenyl or naphthyl radicals may be joined to one another by a chemical single bond via the carbon atoms in the α- and α'-position relative to the phosphorus atom, n is 1, 2 or 3, and Y is cyano, thiocyanato, alkoxy, aryloxy, alkylthio, arylthio, alkylamino, dialkylamino, arylamino or diarylamino.

With regard to the definition of the variables, reference is made here, and also in the embodiments described below, to the statements already made above on the copper(I) complexes of the formula I.

In particular, those copper(I) complexes of the formula Ia are claimed in which

R is alkyl,

Ar is phenyl or naphthyl, each of which is optionally substituted by from one to three radicals selected from the group consisting of alkoxy, alkylamino, dialkylamino, alkoxycarbonyl, halogen, cyano, carboxyl and nitro, and the two optionally substituted phenyl or naphthyl radicals may be joined to one another by a chemical single bond via the carbon atoms in the α- and α'-position relative to the phosphorus atom, n is 1 or 2, and Y is alkoxy, aryloxy, alkylthio, arylthio, alkylamino, dialkylamino, arylamino or diarylamino.

In the particularly preferred copper(I) complexes of the formula Ia,

R is alkyl,

Ar is phenyl or naphthyl, n is 1 or 2, and

Y is alkoxy, aryloxy, alkylthio, arylthio, alkylamino, dialkylamino, arylamino or diarylamino.

The present application further provides novel copper(I) complexes of the formula Ib

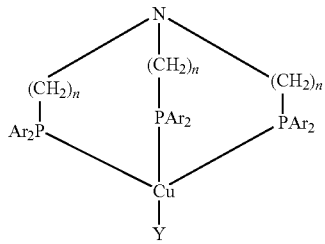

(Ib)

where

Ar is phenyl or naphthyl, each of which is optionally substituted by from one to three radicals selected from the group consisting of alkoxy, alkylthio, alkylamino, dialkylamino, alkoxycarbonyl, alkoxysulfonyl, halogen, cyano, carboxyl, hydroxysulfonyl and nitro, and the two optionally substituted phenyl or naphthyl radicals may be joined to one another by a chemical single bond via the carbon atoms in the α- and α'-position relative to the phosphorus atom, n is 1, 2, 3, and Y is halogen, cyano, thiocyanato, alkoxy, aryloxy, alkylthio, arylthio, alkylamino, dialkylamino, arylamino or diarylamino.

In particular, copper(I) complexes of the formula Ib are claimed in which

Ar is phenyl or naphthyl, each of which is optionally substituted by from one to three radicals selected from the group consisting of alkoxy, alkylamino, dialkylamino, alkoxycarbonyl, halogen, cyano, carboxyl and nitro, and the two optionally substituted phenyl or naphthyl radicals may be Joined to one another by a chemical single bond via the carbon atoms in the α- and α'-position relative to the phosphorus atom, n is 1 or 2, and Y is halogen, cyano, thiocyanato, alkoxy, aryloxy, alkylthio, arylthio, alkylamino, dialkylamino, arylamino or diarylamino.

In the particularly preferred copper(I) complexes of the formula Ib,

Ar is phenyl or naphthyl, n is 1 or 2, and

Y is halogen, cyano, thiocyanato, alkoxy, aryloxy, alkylthio, arylthio, alkylamino, dialkylamino, arylamino or diarylamino.

The copper complexes of the formulae Ia and Ib can be synthesized based on the complexes already known. Reference is also made to the remarks already made with regard to the synthesis of the copper(I) complex of the formula I and the reference to the relevant literature cited at the outset.

EXAMPLE 0.102 g (0.54 mmol) of dry copper(I) iodide was dissolved in 20 ml of acetonitrile and admixed with 0.320 g (0.51 mmol) of 1,1,1-tris(diphenylphosphinomethyl)ethane in solid form. The mixture was allowed to boil under reflux for 20 minutes. The resulting white precipitate was filtered off with suction, washed with acetonitrile and diethyl ether and dried. The solid exhibited blue emission at a wavelength in the emission maximum of 465 nm.

The electroluminescence of the example compound (emitter) was measured in the

ITO/α-NPD/Cu(tripod)I/BCP/LiF/Al layer structure without matrix material for the emitter.

In this structure:

| | |
|---|---|
| ITO: | indium tin oxide |
| α-NPD: | 4,4'-bis[N-(1-Naphthyl)-N-phenylamino]biphenyl |
| Cu(tripod)I: | example compound (emitter) |
| BCP: | 2,9-dimethyl-4,7-diphenyl-1,10-phenanthroline |
| LiF: | lithium fluoride |
| Al: | aluminum |

The emission maximum of the emitter for this layer structure was at 526 nm.

What is claimed is:

1. A method for preparing an organic light-emitting diode, comprising:

forming at least one layer of the diode to contain at least one copper(I) complex having the formula I

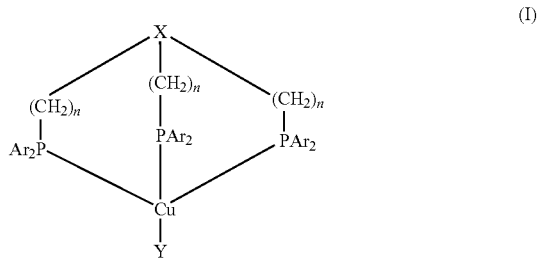

(I)

wherein

X is nitrogen or a C—R group,

R is alkyl or aryl,

Ar is phenyl or naphthyl, optionally substituted by from one to three radicals selected from the group consisting of alkoxy, alkylthio, alkylamino, dialkylamino, alkoxycarbonyl, alkoxysulfonyl, halogen, cyano, carboxyl, hydroxysulfonyl and nitro, and the two optionally substituted phenyl or naphthyl radicals may be joined to one another by a chemical single bond via the carbon atoms in the α- and α'-position relative to the phosphorus atom, n is 1, 2 or 3, and Y is halogen, cyano, thiocyanato, alkoxy, aryloxy, alkylthio, arylthio, alkylamino, dialkylamino, arylamino or diarylamino.

2. The method according to claim 1, wherein n is 1 or 2.

3. The method according to claim 1, wherein X is C—R.

4. The method according to claim 3, wherein R is alkyl.

5. The method according to claim 1, wherein the at least one layer of the diode is selected from the group of layers consisting of a light emitting layer and a blocking layer.

6. The method according to claim 1, wherein the at least one layer formed containing the copper(I) complex having the formula I is the light emitting layer.

7. The method according to claim 6, wherein the formed light emitting layer contains only the copper(I) complex having the formula I.

8. An organic light-emitting diode, comprising:
an anode;
a hole-transporting layer;
a light-emitting layer;
an electron-transporting layer; and
a cathode; wherein
at least one of the layers comprises a copper(I) complex having the formula I

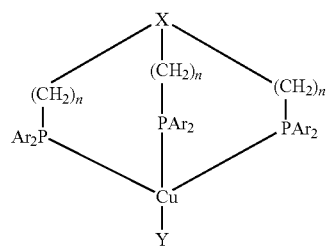

(I)

wherein

X is nitrogen or a C—R group,

R is alkyl or aryl,

Ar is phenyl or naphthyl, optionally substituted by from one to three radicals selected from the group consisting of alkoxy, alkylthio, alkylamino, dialkylamino, alkoxycarbonyl, alkoxysulfonyl, halogen, cyano, carboxyl, hydroxysulfonyl and nitro, and the two optionally substituted phenyl or naphthyl radicals may be joined to one another by a chemical single bond via the carbon atoms in the α- and α''-position relative to the phosphorus atom, n is 1, 2 or 3, and Y is halogen, cyano, thiocyanato, alkoxy, aryloxy, alkylthio, arylthio, alkylamino, dialkylamino, arylamino or diarylamino.

9. The light emitting diode according to claim 8, wherein the at least one layer comprising the copper(I) complex having formula I is the light-emitting layer.

10. The light-emitting diode according to claim 9, wherein the light-emitting layer consists of the copper(I) complex having the formula I.

11. A stationary visual display unit comprising an organic light-emitting diode according to claim 8.

12. The light-emitting diode according to claim 8, further comprising: a blocking layer; wherein the blocking comprises a copper(I) complex having the formula I.

13. A copper(I) complex of formula Ia

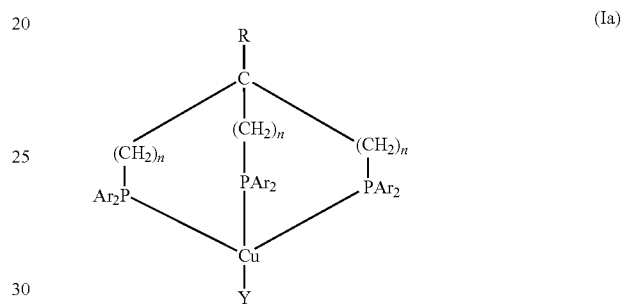

(Ia)

where

R is alkyl,

Ar is phenyl or naphthyl, each of which is optionally substituted by from one to three radicals selected from the group consisting of alkoxy, alkylamino, dialkylamino, alkoxycarbonyl, halogen, cyano, carboxyl and nitro, and the two optionally substituted phenyl or naphthyl radicals may be joined to one another by a chemical single bond via the carbon atoms in the α- and αa'-position relative to the phosphorus atom, n is 1 or 2, and Y is alkylamino, dialkylamino, arylamino or diarylamino.

14. A copper(I) complex of the formula Ia according to claim 13 where

R is alkyl,

Ar is phenyl or naphthyl, n is 1 or 2, and

Y is alkylamino, dialkylamino, arylamino or diarylamino.

* * * * *